United States Patent [19]

King et al.

[11] Patent Number: 4,536,711
[45] Date of Patent: Aug. 20, 1985

[54] METHOD AND APPARATUS FOR MEASURING FLOW IN A PIPE OR CONDUIT

[75] Inventors: James D. King; Erroll S. Riewerts, both of San Antonio, Tex.

[73] Assignee: Southwest Research Institute, San Antonio, Tex.

[21] Appl. No.: 491,868

[22] Filed: May 5, 1983

[51] Int. Cl.³ .............................................. G01R 33/08
[52] U.S. Cl. ..................................... 324/306; 324/307
[58] Field of Search ...................... 73/861.05; 324/300, 324/306, 307, 311, 310, 309, 318

[56] References Cited

U.S. PATENT DOCUMENTS

| | | | |
|---|---|---|---|
| 3,473,108 | 10/1969 | McCormick | 73/861.05 |
| 3,573,607 | 4/1971 | Whitesel | 324/306 |
| 4,110,680 | 8/1978 | Bergmann | 324/306 |

*Primary Examiner*—Michael J. Tokar
*Attorney, Agent, or Firm*—Gunn, Lee & Jackson

[57] ABSTRACT

This method and apparatus is directed to measuring flow velocity of a flowing solid or fluid in a pipe. In the preferred and illustrated embodiment, a single magnet is utilized to impress a magnetic field on the flow, the field having a gradient. A concentrically arranged detection coil is positioned in the field and is connected with a nuclear magnetic resonance (NMR) or electron magnetic resonance (EMR) detection apparatus. A segment of the material moves through the magnetic field. The frequency of a the magnetic resonance signal emitted by the nuclei or electron changes proportionate to field intensity. In a fixed gradient, the time rate of change of the emitted NMR or EMR frequency signal is a linear function of flow velocity. This apparatus provides a measure of flow velocity by interrogating with pulses thereby obtaining a frequency dependent signal. The approach has the advantage of utilization of a single coil and yields measurements which are independent of density or filling factor and also independent of elemental couplings identified as $T_1$ and $T_2$.

39 Claims, 9 Drawing Figures

FIG. 7 FLOW VELOCITY PROFILE

FIG. 8 DETECTED MAGNETIC RESONANCE FREQUENCY SPECTRUM

FIG. 9

METHOD AND APPARATUS FOR MEASURING FLOW IN A PIPE OR CONDUIT

BACKGROUND OF THE DISCLOSURE

This invention was made under U.S. Government Contract No. DE-AC01-79ET15465 and the United States Government has a nonexclusive, nontransferable, irrevocable, paid-up license to practice or have practiced for or on behalf of the United States, this invention throughout the world.

This invention is directed to a method and apparatus for determining the flow velocity of materials typically in a pipe. Consider a pipe formed of non-ferromagnetic materials. Such a pipe can be used to deliver flowing fluids or solids. The rate of flow is an important measurement to be obtained by this invention. This invention is able to provide a measure of the rate of flow of the flowing materials which are independent of the density or filling factor within the pipe. Moreover, the measurement is independent of characteristic magnetic resonance relaxation time constants known as $T_1$ and $T_2$. $T_1$ is the spin-lattice relaxation time and $T_2$ is the spin-spin relaxation time.

This invention utilizes only a single magnet. A magnet forming a magnetic field transverse of the pipe is utilized, the magnet being constructed and arranged to form a magnetic field having a gradient. The gradient introduces the flowing material to a field intensity which is relatively high and which decreases in linear fashion to a lesser value. A segment of the flowing material is exposed at a given instant to this magnetic field. As will be understood, there is a relationship between the flowing segment velocity, field intensity, and frequency at which an NMR or EMR signal might be expected. As the segment of material (resembling a transverse slice enclosed by the pipe) moves through the magnetic field, the frequency of the NMR or EMR signal expected from the flowing material will change. If the field gradient is linear, the frequency change is proportionate to that. Accordingly, the preferred embodiment of this disclosure utilizes a fixed gradient magnetic field. This preferred arrangement yields a time rate of change of the emitted NMR or EMR echo pulse proportionate to flow velocity.

Consider the instance where the flow velocity is doubled. The frequency shift of the EMR or NMR signal over a given time interval is twice the shift encountered with the first flow velocity. The measurement of flow velocity is achieved independent of elemental-matrix characteristic times $T_1$ and $T_2$, and is also independent of the density of the flowing material, or the filling factor of the flowing material in the pipe.

One of the desirable techniques of obtaining the data from the flowing sample is the pulse echo shift in time or frequency. One approach involves contrasting the frequency of the NMR or EMR echo response signal with a reference frequency signal. The shift in frequency of the response obtained is measured. There is separately a shift in the relative time position of the echo obtained from transmitted pulses, and this shift in time has significance.

It has been discovered that the frequency of the echo decreases and the delay time of the echo will also decrease when the flowing material passes through a negative gradient magnetic field. A negative gradient is defined as a field which is decreased from a higher intensity to a lower intensity. If the field has a positive gradient, the frequency of the echo and the echo delay time both increase as a function of flow velocity. From this arrangement, and for a given field gradient, the frequency shift of the echo or echo delay time shift indicate flow velocity in the pipe or conduit.

Accordingly, this invention utilizes to advantage a magnetic field which has either a positive or negative gradient. Moreover, the output is found in frequency shift in the echo or time shift in the echo. Either shift can be used to indicate the flow velocity.

Another factor which impacts the output signal is the density of the material flowing in the pipe. This is more or less fixed with a flowing liquid such as petroleum products, refined chemicals and the like. However, flow density can vary markedly with a flowing gas and with flowing solids as in a coal pipeline. The amplitude of the NMR or EMR signal is proportionate to flow density. For instance, in a selected pipeline delivering natural gas of a fixed hydrocarbon mixture, an increase in pressure provides a proportionate increase in density. If the pressure is doubled, the density is approximately doubled. This manifests itself in the amplitude of the output signal. As will be understood, measurement of the NMR or EMR output signal amplitude is highly advantageous.

In one embodiment of this apparatus, two signal processing channels are included to detect the frequency shift in the form of a phase shift. The received signal is mixed with the transmitted signal for detection of frequency shift. One channel is provided with the transmitted signal while the other channel is provided with the transmitted signal after a 90° phase shift. Both channels are identical thereafter, including mixers, low pass filters, sample and hold amplifiers. The amplifiers output to analog to digital converters. In turn, the two channels are then both input to an arithmetic processor which forms ratios (and hence trignometric functions) of the synchronously detected input digital words. These ratios are then provided to scalers. Two separate time separated signals are output by the arithmetic processor, each provided to a scaler, and they are then input to an adder. The adder outputs the signal represented by the sum (or difference) of the two input signals, and that is in turn proportional to the flow velocity.

An alternate circuit is provided with the NMR or EMR received signal. After sampling through a sample and hold amplifier, it is output to a low pass filter and then input to a frequency comparator. The frequency comparator is provided with a signal of fixed frequency. The shift as indicated by the comparator is then related to velocity.

In many cases the flow velocity is not uniform across the diameter of a pipe or other flow containment device but it is a distribution of velocities. Some flowing material may be moving at a faster velocity than other moving material. This distribution of velocities and the amount of material flowing at each velocity is measurable by the subject invention as a distribution in the frequency content in the detected NMR or EMR signals. The amplitudes of the compounds of the frequency spectrum are proportional to the amount of material flowing at the corresponding velocities. As an illustrative example, if the flow is made up of material flowing at two velocities ($V_1$ and $V_2$), there will be two corresponding frequency components in the detected magnetic resonance signals produced by the flowing material. The amplitude of each frequency component will be proportional to the amount of material moving at that flow velocity. In typical flow in a pipe, the flow velocity is distributed over a range $V_1$ and $V_2$ and the corresponding magnetic resonance frequency spectrum extends over a frequency range $F_1$ to $F_2$ with an amplitude distribution proportional to the material distribution flowing at each velocity.

Many advantages and features of the present apparatus will be noted. In the main, the output signals are in digital form. Being in digital form, they are more readily handled, scaled upwardly to accommodate scale factors, and recorded. Moreover, the flow velocity apparatus is made independent of characteristic times $T_1$ and $T_2$. It is also independent of fill factor or density. The only requirement is that the volume of the material be sufficient in light of signal requirement to overcome noise. This is a practical factor modified by increasing the gain of the receiver to reduce noise. For instance, the signal amplitude can be changed by increasing the number of turns in the coils for the transmitter and receiver.

This apparatus particularly works well by tuning to particular elements or unpaired electrons in the flowing compound. One such element is hydrogen. An alternate is the unpaired electrons associated with the carbon of coal. By measuring the velocity of the hydrogen or carbon, inevitably, the velocity of the entire flowing mass is measured. The frequency of the system is thus set to excite either hydrogen or carbon in the preferred embodiment, and the velocity of that element (and hence the compound which includes the element) is then measured. Alternately, other elements can be measured, typical examples being sodium or chemically bound flourine.

BRIEF DESCRIPTION OF THE DRAWINGS

So that the manner in which the above recited features, advantages and objects of the present invention are attained and can be understood in detail, more particular description of the invention, briefly summarized above, may be had by reference to the embodiments thereof which are illustrated in the appended drawings.

It is to be noted, however, that the appended drawings illustrate only typical embodiments of this invention and are therefore not to be considered limiting of its scope, for the invention may admit to other equally effective embodiments.

DETAILED DESCRIPTION OF THE PREFERRED EMBODIMENT

Figure 1:
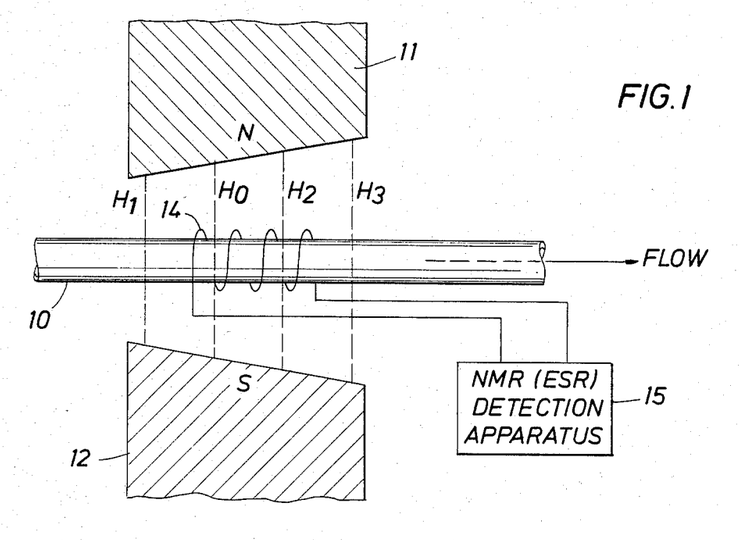
FIG. 1 is a view showing installation of a magnet and detection coil adjacent to a flowing pipeline for measuring the velocity of material in the pipeline.

Attention is first directed to FIG. 1 of the drawings. In FIG. 1, the numeral 10 identifies a pipe or conduit which carries a flowing fluid which is to be tested for velocity. At this portion, the pipe 10 has some material flowing in it, the material typically being particulate solid matter in gas such as pulverized coal pneumatically transported into a combustion chamber, or is a pipeline for petroleum products. The invention is also adapted to be used with flowing gasses of various pressures. The portion of the pipeline 10 shown in FIG. 1 is preferably made of nonmagnetic material so that lines of flux pass through the pipeline 10.

A magnet including a north pole piece 11 is positioned opposite a south pole piece 12. The magnet is shown tapered so that the gap between the poles increases. The field intensity is maximum at the left where the flowing material first encounters the field. It is preferable to define the field impinging on the pipe 10 with a negative gradient, that is, maximum field intensity is at the left hand edge of the field and reduced field intensity is at the right hand side of FIG. 1. To this end, the symbol $H_o$ indentifies the resonant field intensity. $H_1$ identifies the maximum magnetic field intensity. Additional field intensities are defined at $H_2$ and $H_3$. Preferably, the field has a linear gradient. That is, the field intensity decreases in regular fashion, for instance, through the utilization of tapered faces as exemplified at 11 and 12 in FIG. 1. A negative gradient is associated with maximum intensity at the left and decreasing intensity to the right. A positive gradient is the reverse arrangement.

The intensity of interest is the intensity at $H_o$. This is the intensity which is related to the frequency of a transmitted pulse delivered through a detection coil 14. The coil 14 is arranged at right angles to the magnetic field. There is an interplay between a selected element in the material flowing through the pipe 10. This interplay is either EMR or NMR originated to form an output signal which is observed in the detection coil 14. That signal is provided to apparatus identified at 15. The apparatus 15 is depicted either in FIGS. 5 or 6 as will be described hereinbelow.

Figure 2:
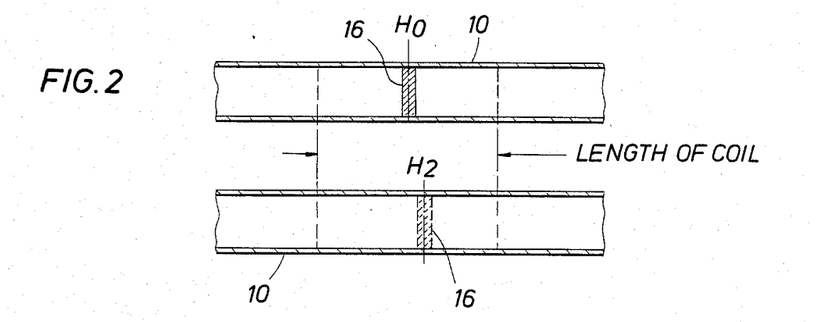
FIG. 2 is a view showing graphically a segment of material in the pipeline of FIG. 1 which is excited by a transmitter pulse, and which is thereafter moved in the pipe to a new location at which time an echo signal is formed.

Attention is momentarily directed to FIG. 2 of the drawings. In FIG. 2, the numeral 16 identifies a segment of flowing material in the pipeline. It is presumed that the material is flowing in the pipe 10 substantially without turbulence, at least in the illustrated portion. There is therefore a cylindrical segment 16 which is the flowing material at the particular field intensity identified by $H_o$. That particular segment 16 is irradiated by the transmitted pulse. The transmitted pulse is from the coil 14. The transmitted pulse field impinges on all the material within the coil but only interacts strongly with the segment 16, the transmitter frequency and the field intensity being related to yield an NMR or EMR response.

The width of the field in FIG. 2 is equal to the width of the pole piece 11 shown in FIG. 1. The material 16 is exposed to a magnetic field at various locations along the pipe. FIG. 2 includes two views, the two views being identical except that the second view shows the material 16 after the passage of time whereby the material 16 has moved. The displacement to the right is the distance travelled. Moreover, this is the position of the slug of material at the time that an echo pulse is returned to the detection coil 14 as a result of the transmitted pulses. While turbulence is potentially a problem, the segment 16 is relatively well defined and defusion of the segment 16 in the short interval illustrated in FIG. 2 is relatively insignficant. Accordingly, the material 16 is well defined when first irradiated and when the echo pulse is created and returned to the detection apparatus 15.

Figure 3:
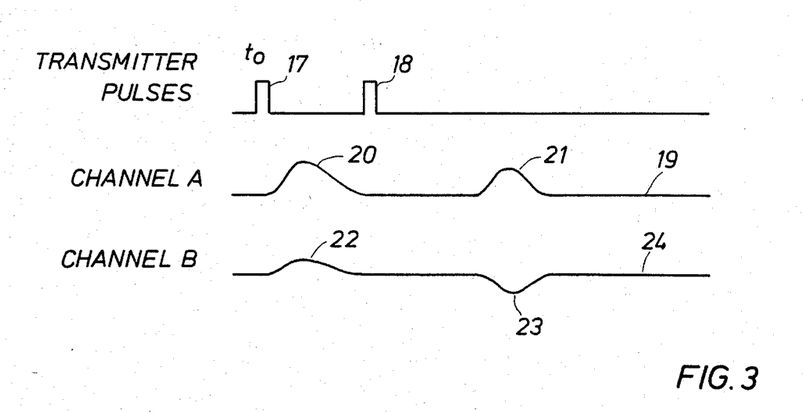
FIG. 3 is an NMR signal sampling sequence showing two channels of output data for use with the circuitry shown in FIG. 5.

Continuing on with the description, attention is next directed to FIG. 3 of the drawings. In FIG. 3, a timing chart beginning at some arbitrary time (time=zero) is included. The transmitter for the equipment to be described forms transmitted pulses. Referring to FIG. 3, there is first transmitted pulse 17 and a second transmitted pulse 18. The two pulses are arbitrarily of equal amplitude and duration. These are pulses of RF energy at a specific frequency. That frequency is proportionate to field intensity $H_o$ to produce electromagnetic resonance with a selected nuclear specie or with unpaired electrons. The pulses 17 and 18 are at the selected frequency and are transmitted at a suitable amplitude to adequately excite the material 16. An NMR echo is initiated by the pulses 17 and 18. The NMR echo pulse is thus generated by two bursts of several cycles at the requisite frequency to relate to the imposed magnetic field $H_o$. The two pulses are about five microseconds in duration and are separated by about twenty-three microseconds. Needless to say, the spacing and pulse duration can be varied for optimum results. These are varied dependent on field intensity(s) and the spacing requisite for the pulses as determined by the characteristic spin-spin relaxation time $T_2$.

FIG. 3 shows at 19 an output signal on receiver channel A. The receiver signal 19 includes a first peak 20 and a second peak 21. The timing and spacing of the peaks 20 and 21 are typical. As will be understood, the first peak 20 comprises the free induction decay (FID) response, and the second peak 21 comprises the pulse echo response. FIG. 3 further illustrates a peak 22 from channel B of the detected received data obtained in phase quadrature with channel A. The second channel outputs a second peak 23, the first being the FID response and the second peak being the echo response. They are in the second channel of data at 24. It will be observed that the responses 20 and 22 occur at approximately the same instant and the echos 21 and 23 occur at approximately the same instant. The two channels are identified as channels A and B for identification purposes.

Figure 5:
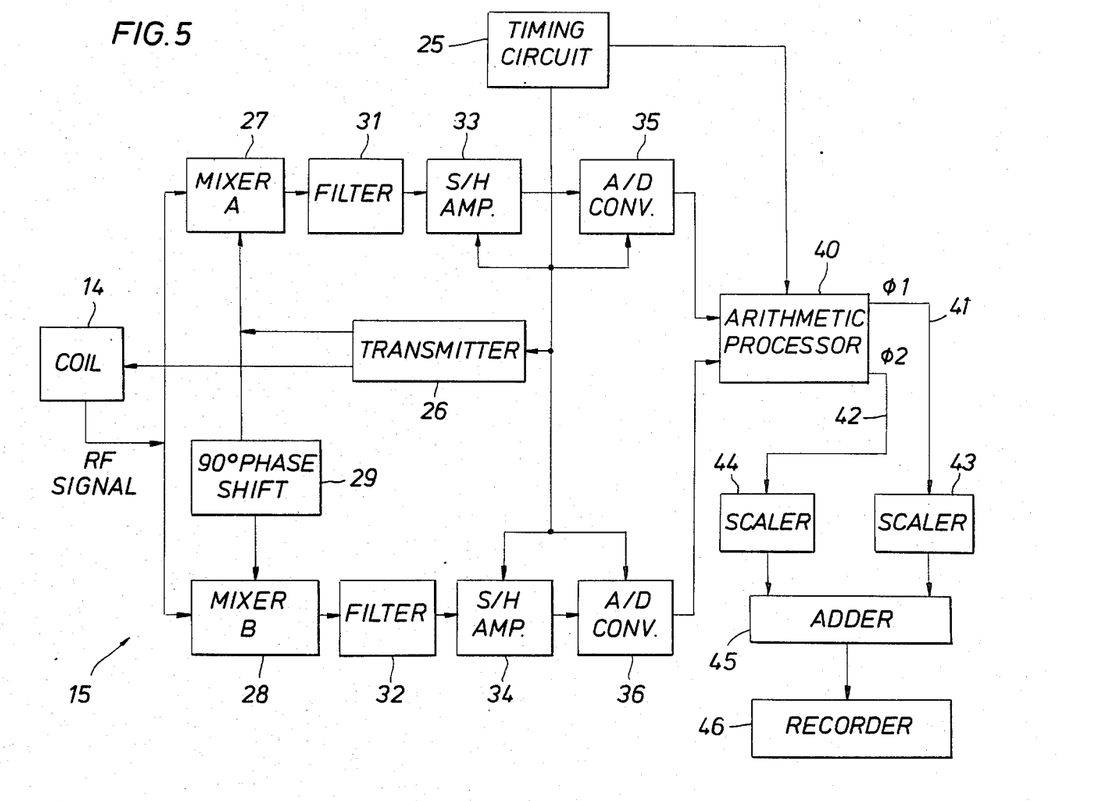
FIG. 5 is a schematic block diagram of a circuit comprising NMR or EMR detection circuitry forming a flow velocity output.

Attention is next directed to FIG. 5 of the drawings which shows apparatus forming the signals illustrated in FIG. 3. The entire apparatus in FIG. 5 is identified by the numeral 15 and is the NMR or EMR detection apparatus earlier illustrated in FIG. 1 of the drawings.

In FIG. 5 of the drawings, a timing circuit 25 forms sequenced signals for operation of the circuitry shown. It forms a timed signal for operation of the transmitter 26. The transmitter 26 is connected with the detection coil 14 to transmit pulses of the proper amplitude and frequency. Such pulses are input to the coil and transmitted by it to produce an electromagnetic field in the flowing material. The coil 14 also serves as a receiver coil, thereby forming received FID signals and echo pulses. Such received pulses are output by the coil 14, amplified and input to a mixer 27. The mixer 27 is duplicated by a similar mixer 28. They form separate channels A and B through the equipment. In addition, a portion of the transmitted signal is a reference input to the mixer 27. Needless to say, the relative amplitude of the reference signals are brought more or less equal by means of suitable attenuators to reduce the transmitted pulse amplitude. As appropriate, an RF amplifier is interposed between the coil 14 and the mixer 27 to boost the received signal to a suitable amplitude. The transmitted signal is input to the mixer 28 after the reference signal passes through a 90° phase shift circuit 29. The phase shift circuit 29 thus assures that channels A and B are out of phase by 90°.

The mixer 27 forms an output for a low pass filter 31. The mixer 28 is connected to a low pass filter 32. The filters form outputs for sample and hold amplifiers 33 and 34. They are triggered by timed signals from the timer 25. The timer 25 controls sampling of signals from channels A and B at selected times for encoding by the analog to digital converters 35 and 36. These devices digitize in timed sequence the sampled analog values input from the filters to the amplifiers 33 and 34. These signal segments are amplified, peak values digitized and the digital signals are then output from the converters 35 and 36.

The numeral 40 identifies an arithmetic processor. It is provided with input words in digital form from the two signals. Referring again to FIG. 3, the first inputs are the peaks 20 and 22, and these are digitized. The arithmetic processor forms a signal which is an angle given by the arc tangent of the ratio of the two input values. This forms a first output signal which is on the conductor 41 and is a measure of the phase angle of the sampled FID signal relative to the transmitted signal. The peaks 21 and 23 occur later in time as shown in FIG. 3; they are also processed though the channels A and B to form a second ratio. This ratio is used to provide an angle which is given by the arc tangent of the ratio. That output signal is on the conductor 42 is a measure of the phase angle of sample echo signal relative to the transmitted signal. The conductor 41 is input to a scaler 43. In like fashion, the output on the conductor 42 is input to a scaler 44. The scalers 43 and 44 apply suitable scale values to the two input signals (recalling that they are in digital form at this juncture) and the two digital output signals are then supplied to an adder circuit 45. The adder circuit adds the two with proper sign to determine the phase difference between the FID and the echo signals and outputs them to a flow velocity recorder 46. Through the implementation of suitable scale values, the flow velocity is indicated in correct and proper scale.

The velocity is proportional to the sum of the two signals on the conductors 41 and 42. These signals are added or subtracted dependent on the direction of field gradient. Thus, with proper scaling at the scalers 43 and 44, the output values are directly added or subtracted (dependent on sign which is in turn dependent on gradient) and the flow velocity is directly indicated in suitable units such as feet per second, meters per minute, etc.

As described at this juncture, the system utilizes the frequency shift which formed by material flow and the related change in the strength of the magnetic field at the time of occurrence of the FID or the echo signals. There is an interval of time occurring between the transmitted pulse 17 and the formation of the echo pulse 21. In other words, the relative movement of the sample to an altered magnetic field intensity causes a change in the echo pulse compared to the echo pulse occurring if the magnetic field had constant intensity throughout the flow space. This frequency change is proportionate to the gradient, and given a linear gradient at the magnet, the frequency shift noted in the echo pulse 21 provides data indicative of velocity. The frequency shift may be measured as a phase shift by utilizing the relationship above wherein the velocity equals the sum of the arc tangent of the peak 20 over the peak 22 plus the arc tangent of the peak 21 over the peak 23, then one may readily obtain velocity in properly calibrated units.

The equation is:

$$\text{Velocity} = K[\phi_1 \pm \phi_2]$$

$$\phi_1 = \tan^{-1} 20/22$$

$$\phi_2 = \tan^{-1} 21/23$$

Going back to FIG. 2 of the drawings, the width of the material 16 is in part determined by the time duration and shape of the transmitted pulse, the gradient of the magnetic field shown in FIG. 1, and, to a lesser extent, by the velocity of the material in the pipe 10.

Figure 4:
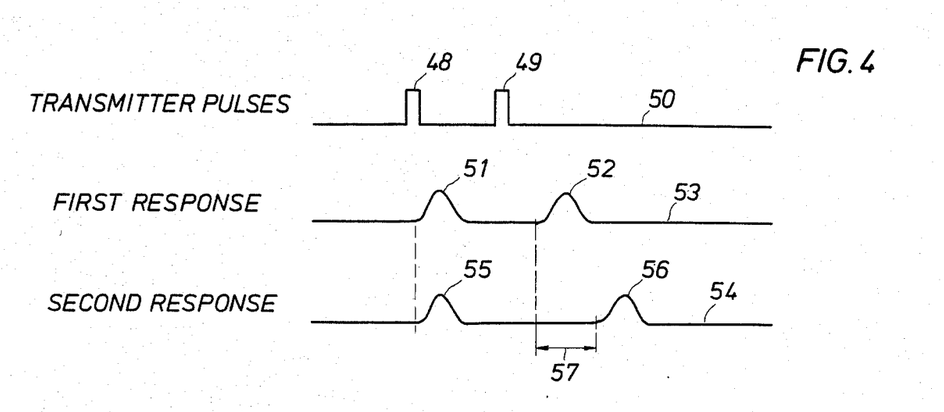
FIG. 4 is a view similar to FIG. 3 showing in timed chart sequence received signals.

In FIG. 4 of the drawings, transmitted pulses 48 and 49 are illustrated in the wave form 50. The first response 51 (the FID signal) is also shown in timed relationship to the transmitted pulse 48. The pulse echo 52 is likewise shown in the wave form 53. In like fashion, a later received wave form 54 incorporates received signals 55 and 56. There is an incremental time shift 57 between the echo pulses 52 and 56. This pulse shift 57 is indicative of velocity in the pipe 10. The time offset 57 is thus proportional to changes in velocity. There is a reference position for the pulse 52 which exists when velocity is zero. Therefore, the time shift 57 is proportional to velocity.

The time offset 57 which is a result of changes in velocity is significant in providing data indicative of velocity; it is harder to measure then the procedure shown in FIG. 3. In FIG. 3, it will be recalled that the sampled signals have the amplitudes at peaks 19, 20, 22, and 23 output by the sample and hold amplifiers under control of the timing circuit 25.

As further shown in FIG. 4, the signals 51, 52, 55 and 56 have a measurable amplitude signal. Amplitudes are proportional to density. Briefly, the amount of material in the interrogated sample 16 determines the amplitude of these output signals. Ordinarily, it is only required that the material 16 be sufficient to provide an output signals of sufficient amplitude to be observed. However, as the quantity of the material 16 including the element of interest is increased, the output signals likewise increase. Through suitable calibration techniques, the signal amplitude of the FID signals 51 and 55, or the echo pulses 52 and 56 can be measured to determine the density of the observed material. Using the dual channel detector featuring phase quadrature channels, the output of each channel is a vector component of the total signal vector. The desired signal amplitude (for density) is the vector magnitude and is equal to the square root of the sum of the squares of the two vector components A and B. The density measurement is reasonably accurate over a limited range, the range being limited between specified density values. Again, this might also relate to a fill factor. Consider the example of pulverized coal carried by pneumatic flow in a pipe. The percentage of particulate coal can be increased to vary the fill factor. The signal amplitude at 58 is thus measured to determine density or fill factor within a specified range.

Figure 6:
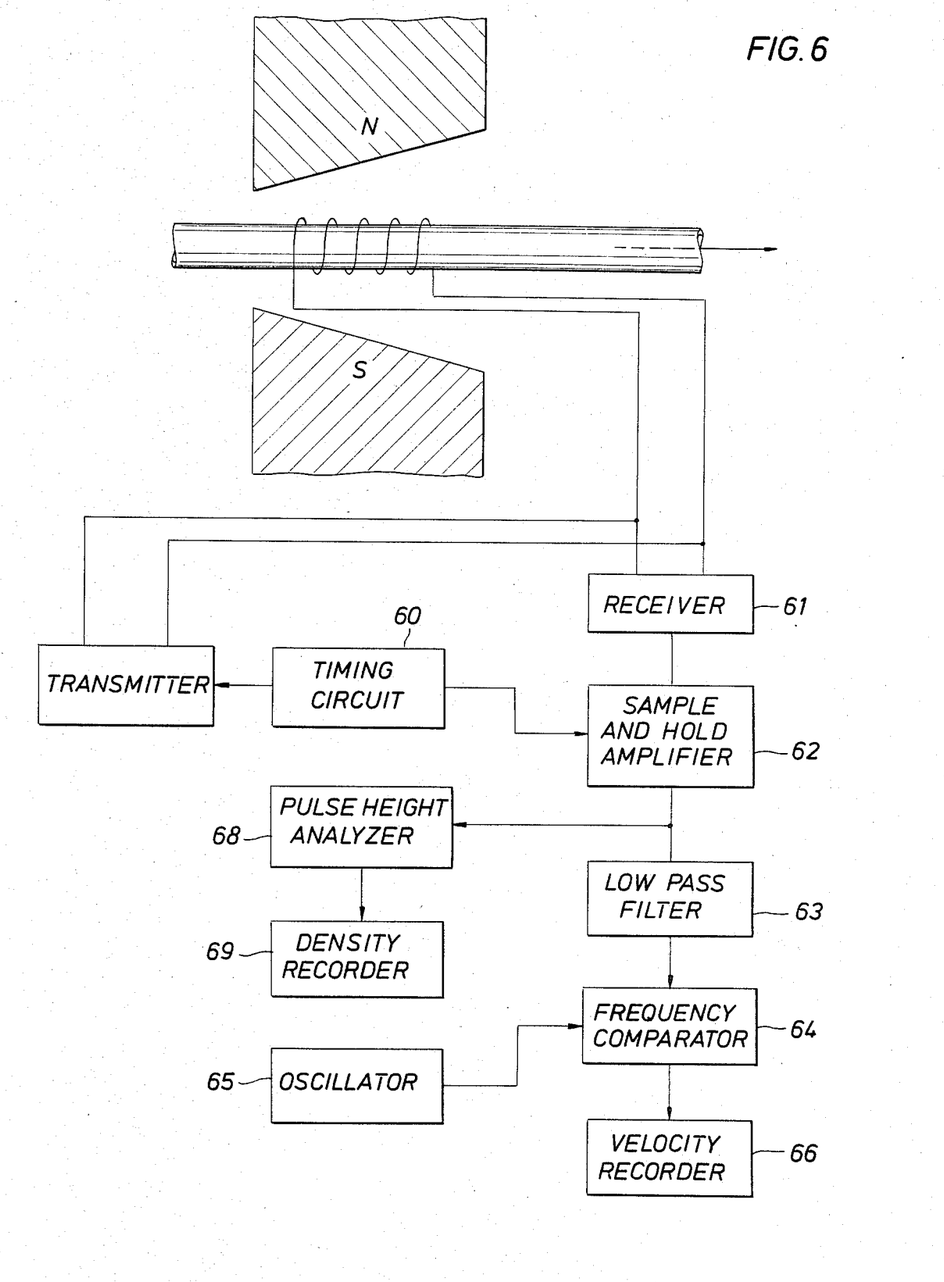
FIG. 6 is a schematic block diagram of an alternate form of circuitry for detecting flow velocity and density.

FIG. 6 shows a circuit which can be used to determine frequency shift and signal amplitude. FIG. 6 depicts a timer circuit 60. The timer circuit provides a signal for control of an NMR receiver 61. The receiver 61 forms FID and echo signals which are input to a sample and hold amplifier 62. It is gated in operation to form an output to a low pass filter 63. The filter 63 forms a signal input to a frequency comparator 64. The frequency comparator is also provided with an input signal from an oscillator 65 which forms a reference. The two signals are compared and the frequency shift is output to a velocity recorder 66. The output signal is proportionate to velocity within a specified range. This velocity encoding in frequency shift is the result of the change in frequency of the NMR echo pulse.

Separate from the velocity output signal just described, the apparatus further includes a pulse height analyzer 68 which is connected to a density recorder 69. The sample and hold circuit forms a sampled output signal indicative of amplitude of the NMR or EMR signal. This signal can be obtained directly from the sample and hold amplifier 62. It is preferable to at least pass through a low pass filter to remove the carrier wave. The amplitude of interest is encoded in the envelope of the carrier. The signal can be passed through an analog digital converter as desired. The density is thus obtained by measuring the amplitude of the pulse 58, thereafter inputting that pulse as measured to the pulse height analyzer and obtaining a relative measure of the pulse height. By proper calibration, the density is then output to the density recorder 69.

Figure 7:
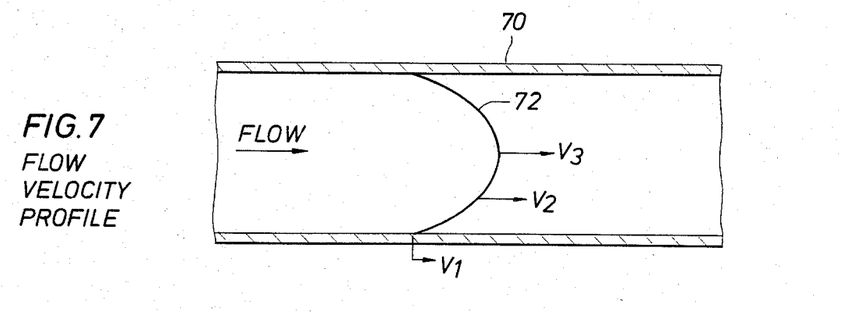
FIG. 7 is a diagram illustrating distribution of flow velocities across a pipe.
Figure 8:
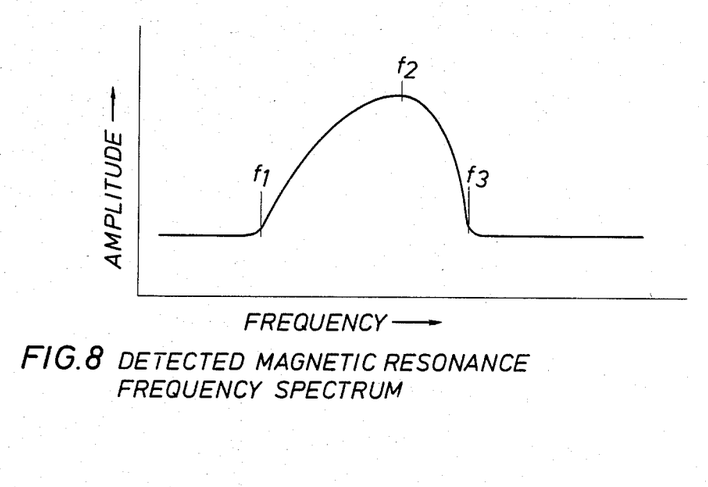
FIG. 8 is a corresponding frequency-amplitude distribution of the detected material flowing in the pipe of FIG. 7.

FIG. 7 illustrates a flow profile wherein the flow velocity of the material flowing in the pipe 70 is not uniform across the diameter of the pipe. A detector coil and associated NMR or EMR detector in the magnetic gradient field as previously described will produce a detected frequency-amplitude spectrum are shown in FIG. 8. In FIG. 8, the frequency of $F_1$ corresponds to the material flowing at velocity $V_1$, $F_2$ to the material flowing at velocity $V_2$, $F_3$ to the material flowing at velocity $V_3$, etc. The amplitude of the detected magnetic resonance signal component of the spectrum at each frequency is proportional to the amount of detected material flowing at the corresponding velocity.

Figure 9:
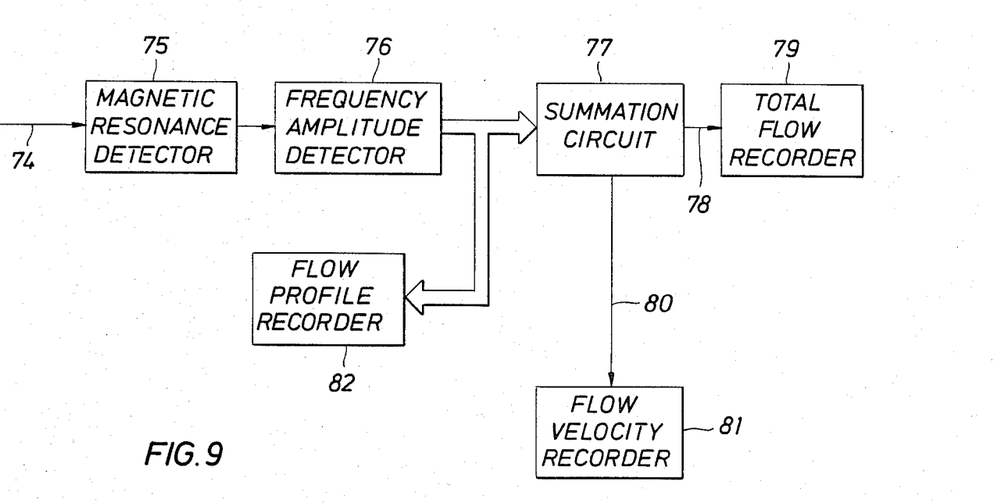
FIG. 9 is a schematic of a circuit for recovery of data exemplified in FIG. 8.

FIG. 9 shows a detector suitable for obtaining frequency spectra data such as illustrated in FIG. 8, and using this data to measure total flow or average flow velocity. The conductor 74 is connected to the sensor coil 14 located about the flow pipe 70 in a magnetic field having gradient in the direction of flow as previously described. The magnetic resonance detector 75 may use transient methods to produce FID and pulse echo signals as previously described, or the detector 75 can be a continuous wave type detector such as is well known and commonly used in EMR and NMR apparatus. The frequency amplitude detector 76 uses the output from the detector 75 to produce an output which is the amplitude versus frequency spectrum of the detected NMR or EMR signal in the gradient magnetic field. The detector 76 can be a frequency discriminator of a type suitable for use with the output signal from the detector 75; or the detector 76 can be a fast Fourier transform computer. Such suitable detectors 76 are well known. The output spectrum is summed in the summation circuit 77 and forms an output on the conductor 78 which is proportional to total flow. The conductor 78 inputs to the total flow recorder 79. The total flow is the sum of the multiple products of the flow velocity and flow density for the full range of the spectrual distribution. A second output conductor 80 is the average flow velocity derived by the summation circuit 77 from the frequency spectrum properly weighted for the amplitude of each frequency component. The detector 76 also provides frequency and amplitude outputs that are displayed or recorded by a recorder 82 to show a plot of the velocity versus amplitude of the flow profile in the pipe 70.

In operation, the device of the present invention is operated particularly for a pipeline delivering a specified product such as natural gas, oil pulverized coal or the like. An assay of the expected product is measured and obtained, typically observing the relative concentration of some element such as hydrogen, carbon or other element in the flowing material. This assists in scaling the system. The gradient is adjusted to assure that the echo pulse is adequately shifted. A gradient of only 5% or 10% will suffice. Even better, a gradient of perhaps 30% or more will assure the formation of a relatively sharp shifted signal.

While the foregoing is directed to the preferred embodiment, the scope is determined by the claims which follows:

What is claimed is:

1. An apparatus for measuring the velocity of flow in a pipe of a material having an adequate population of a selected element comprising:
    (a) magnet means for forming a magnetic field perpendicular to the flow of the element of interest in the pipe, the field having a gradient in the direction of flow;
    (b) coil means forming a field at right angles to the magnetic field formed by said magnet means;
    (c) transmitter means connected to said coil, said transmitter means being adapted to form and apply to said coil means a signal having a frequency related to a first magnetic field intensity to accomplish a resonant relationship between the magnetic field transmitted signal, and the element of interest;
    (d) receiver means for detecting magnetic resonance signals from the element of interest flowing through said coil means, said receiver means forming an output signal of detected signals;
    (e) detector means connected to said receiver means for measuring the change in the detected signals from said receiver means and indicating flow velocity of the element of interest as indicated by the change in the detected signals; and
    (f) timer means for operating said transmitter means to form a pair of spaced transmitted pulses, and wherein said receiver means receives echoes from the element of interest.

2. The apparatus of claim 1 including frequency shift measuring means for determining the frequency shift in the detected signals and indicating the flow velocity therefrom.

3. The apparatus of claim 1 wherein said detector means includes means for measuring the phase of the detected signals and indicating flow velocity therefrom.

4. The apparatus of claim 1 wherein said detector means includes means for measuring the time position of the detected signals and indicating flow velocity therefrom.

5. The apparatus of claim 1 further including means for mixing the received echo pulse in a first channel with the transmitted signal, and a similar second channel wherein the second channel receives the transmitted pulse shifted by 90°, and the two separate channels provide output signals to peak amplitude measuring means, said peak measuring means measuring peak amplitudes from the first channel and peak amplitudes from the second channel, and circuit means provided with the peaks from said first channel and said second channel to form an output given by the ratios thereof which is the arc tangent wherein the arc tangent encodes the flow velocity.

6. The apparatus of claim 1 further including means for mixing the received echo pulse in a first channel with the transmitted signal, and a similar second channel wherein the second channel receives the transmitted pulse shifted by 90°, and the two separate channels provide output signals to measuring means, said measuring means measuring signals from the first channel and the second channel, and circuit means provided with the peaks of said first channel and said second channel to form an output given by the ratios thereof having the form of $\phi_1 + \phi_2$ where $\phi_1$ and $\phi_2$ are both arc tangents.

7. The apparatus of claim 1 wherein said detector means measures the amplitude of the detected signals and determines density proportionate to amplitude within a specified range.

8. The apparatus of claim 7 including a pulse height analyzer comprising said detector means.

9. The apparatus of claim 1 wherein said magnet means is comprised of a pair of pole faces spaced by a gap which increases to form a magnetic field gradient.

10. The apparatus of claim 9 further including a gap adjacent said coil means concentric around a pipe flowing the material.

11. The apparatus of claim 1 including time shift measuring means for measuring the time shift of the echo pulse and indicating the flow velocity therefrom.

12. The apparatus of claim 1 further including mixer means connected to the output of said receiver means, and also including a input thereto from said transmitter means to mix the transmitted and received signals.

13. The apparatus of claim 1 wherein said receiver means detects signals from the element of interest and is connected to provide the detected signal to measuring means for measuring the detected signal proportional to density of the element of interest.

14. The apparatus of claim 1 wherein the detected signal has a frequency spectrum and amplitude range, and including means for detecting amplitude distribution as a function of frequency spectrum to indicate flow velocity and flow density profile of the element of interest.

15. The apparatus of claim 14 including summing means for a multiplicity of frequency and amplitude products corresponding to amplitude distribution and frequency spectrum to indicate the total flow rate.

16. An apparatus for measuring the velocity of flow in a pipe of a material having an adequate population of a selected element, comprising:
    (a) magnet means for forming a magnetic field perpendicular to the flow of the element of interest in the pipe, the field having a gradient in the direction of flow;

(b) coil means forming a field at right angles to the magnetic field formed by said magnet means;

(c) transmitter means connected to said coil, said transmitter means being adapted to form and apply to said coil means a signal having a frequency related to a first magnetic field intensity to accomplish a resonant relationship between the magnetic field transmitted signal, and the element of interest;

(d) receiver means for detecting pulse echo signals from the element of interest flowing through said coil means, said receiver means forming a detected signal encoding the flow of the element of interest;

(e) measuring means for measuring the detected signal and indicating flow velocity of the element of interest; and (f) means for operating said transmitter means to form a pair of spaced transmitted pulses, and wherein said receiver means is operated to receive echoes from the element of interest.

17. The apparatus of claim 16 including frequency shift measuring means for determining the frequency shift in the detected signals and indicating the flow velocity therefrom.

18. The apparatus of claim 16 wherein said detector means includes means for measuring the phase of the detected signals and indicating flow velocity therefrom.

19. The apparatus of claim 16 wherein said detector means includes means for measuring the time position of the detected signals and indicating flow velocity therefrom.

20. The apparatus of claim 16 further including means for mixing the received echo pulse in a first channel with the transmitted signal, and a similar second channel wherein the second channel receives the transmitted pulse shifted by 90°, and the two separate channels provide output signals to peak amplitude measuring means, said peak measuring means measuring peak amplitudes from the first channel and peak amplitudes from the second channel, and circuit means provided with the peaks from said first channel and said second channel to form an output given by the ratios thereof which is the arc tangent wherein the the arc tangent encodes the flow velocity.

21. The apparatus of claim 16 further including means for mixing the received echo pulse in a first channel with the transmitted signal, and a similar second channel wherein the second channel receives the transmitted pulse shifted by 90°, and the two separate channels provide output signals to measuring means, said measuring means measuring signals from the first channel and the second channel, and circuit means provided with the peaks of said first channel and said second channel to form an output given by the ratios thereof having the form of $\phi_1 + \phi_2$ where $\phi_1$ and $\phi_2$ are both arc tangents.

22. The apparatus of claim 16 wherein said detector means measures the amplitude of the detected signals and determines density proportionate to amplitude within a specified range.

23. The apparatus of claim 22 including a pulse height analyzer comprising said detector means.

24. The apparatus of claim 16 wherein said magnet means is comprised of a pair of pole faces spaced by a gap which increases to form a magnetic field gradient.

25. The apparatus of claim 24 further including a gap adjacent said coil means concentric around a pipe flowing the material.

26. A method of determining flow velocity of an element of interest moving along a flow path comprising the steps of:

(a) forming a magnetic field across the flow path, the field having a specified field strength and changing value along the path to create a gradient in the field;

(b) forming first and second RF pulse bursts separated by a period of time for transmission into the flow path and at right angles to the magnetic field to initiate resonant interaction with the element of interest in timed sequence to enable the element of interest to move to a different magnetic intensity;

(c) receiving first and second echo pulses after transmission of the pulse bursts; and (d) measuring the echo pulses for a velocity dependent change resulting from flow of the element of interest.

27. The method of claim 26 wherein the step of measuring the echo pulses includes the step of measuring echo pulse time shift.

28. The method of claim 26 wherein the step of measuring the echo pulses includes the step of measuring echo pulse phase shift.

29. The method of claim 26 wherein the step of measuring the echo pulses includes the step of measuring echo pulse frequency shift.

30. The method of claim 26 wherein the step of measuring the echo pulses includes the step of measuring echo pulse peak amplitude.

31. The method of claim 26 further including the step of changing the magnetic field with a positive gradient.

32. The method of claim 26 further including the step of changing the magnetic field with a negative gradient.

33. The method of claim 26 wherein the product of the measured velocity and the measured flow density are used to provide a measure of the mass flow rate.

34. The method of claim 33 wherein the measure of mass flow rate is time integrated to provide a measure of total flow.

35. The apparatus of claim 1 wherein the product of the measured velocity and the measured flow density are used to provide a measure of the mass flow rate.

36. The apparatus of claim 1 wherein the measure of mass flow rate is time integrated to provide a measure of total flow.

37. The apparatus of claim 16 wherein the product of the measured velocity and the measured flow density are used to provide a measure of the mass flow rate.

38. The apparatus of claim 16 wherein the measure of mass flow rate is time integrated to provide a measure of total flow.

39. An apparatus for measuring the velocity of flow in a pipe of a material having an adequate population of a selected element comprising:

(a) magnet means for forming a magnetic field perpendicular to the flow of the element of interest in the pipe, the field having a gradient in the direction of flow;

(b) coil means forming a field at right angles to the magnetic field formed by said magnet means;

(c) transmitter means connected to said coil, said transmitter means being adapted to form and apply to said coil means a signal having a frequency related to a first magnetic field intensity to accomplish a resonant relationship between the magnetic field transmitted signal, and the element of interest;

(d) receiver means for detecting magnetic resonance signals from the element of interest flowing through said coil means, said receiver means forming an output signal of detected signals;
(e) detector means connected to said receiver means for measuring the change in the detected signals from said receiver means and indicating flow velocity of the elemnt of interest as indicated by the change in the detected signals, the detected signals having a specified frequency spectrum and amplitude range; and
(f) frequency responsive means for detecting amplitude distribution as a function of the specified frequency spectrum to indicate flow velocity and flow density profile of the element of interest.

* * * * *